United States Patent [19]

Kobayashi et al.

[11] Patent Number: 5,075,406
[45] Date of Patent: Dec. 24, 1991

[54] PROCESS FOR REFINING 1,3-DIMETHYL-2-IMIDAZOLIDINONE

[75] Inventors: Tadashi Kobayashi; Mitsuo Wada; Shouzi Obuchi, all of Omuta; Hiroshi Takayanagi, Yokohama, all of Japan

[73] Assignee: Mitsui Toatsu Chemicals, Inc., Tokyo, Japan

[21] Appl. No.: 626,692

[22] Filed: Dec. 13, 1990

Related U.S. Application Data

[62] Division of Ser. No. 319,698, Mar. 7, 1989, Pat. No. 5,011,936.

[30] Foreign Application Priority Data

| Mar. 8, 1988 | [JP] | Japan | 63-52493 |
| Apr. 1, 1988 | [JP] | Japan | 63-78186 |
| Feb. 8, 1989 | [JP] | Japan | 1-27373 |

[51] Int. Cl.$^5$ ............................................. C08G 18/20
[52] U.S. Cl. ...................................................... 528/53
[58] Field of Search ........................................... 528/53

[56] References Cited

U.S. PATENT DOCUMENTS

| 2,993,906 | 7/1961 | Sprenger et al. | 260/309.7 |
| 4,701,555 | 10/1987 | Young et al. | 564/38 |
| 4,795,795 | 1/1989 | Kouno et al. | 528/53 |

FOREIGN PATENT DOCUMENTS

| 215964 | 1/1987 | European Pat. Off. . |
| 175170 | 4/1982 | Japan . |
| 90517 | 1/1986 | Japan . |
| 172862 | 7/1986 | Japan . |
| 204218 | 10/1986 | Japan . |

*Primary Examiner*—Maurice J. Welsh
*Attorney, Agent, or Firm*—Fisher, Christen & Sabol

[57] ABSTRACT

The present invention is directed to a refining process for removing impurities from 1,3-dimethyl-2-imidazolidinone (DMI) by the use of a composite salt; and a process for preparing an aromatic polyamide having a high polymerization degree from an aromatic diisocyanate and an aromatic dicarboxylic acid by using, as a reaction solvent, DMI purified by the above-mentioned process.

18 Claims, No Drawings

PROCESS FOR REFINING 1,3-DIMETHYL-2-IMIDAZOLIDINONE

This is a division of application Ser. No. 07/319,698, filed Mar. 7, 1989, now U.S. Pat. No. 5,011,936.

BACKGROUND OF THE INVENTION

1. Field of the Invention

The present invention relates to a process for refining 1,3-dimethyl-2-imidazolidinone (hereinafter referred to simply as "DMI") and a process for preparing an aromatic polyamide from an aromatic diisocyanate and an aromatic dicarboxylic acid by using DMI, as a reaction solvent, which has been refined by the above-mentioned process.

2. Description of the Prior Art

DMI which is a five-membered compound containing nitrogen is utilized as a solvent for various reactions, because DMI is a high-boiling non-protonic polar compound having less toxicity and excellent properties.

Manufacturing processes of DMI are disclosed in Japanese Patent Laid-open Publication Nos. 175170/1982 and 172862/1986 and elsewhere, and high-purity DMI is obtained finally by distillation and is on the market.

However, even commercially available high-purity DMI contains not only water but also protonic compounds which are by-products such as biuret, urea, acetamide and N-methylformamide (hereinafter referred to simply as "NMF") as impurities in an amount of 50 to 1,000 ppm. The contents of these impurities depend upon manufacturing conditions of DMI and subsequent distillation conditions.

When DMI is used together with a raw material such as an isocyanate which easily reacts with the protonic compound, a satisfactory effect cannot be obtained at times.

Particularly, in the case that commercially available DMI is used as a polymerization reaction solvent for, e.g., an isocyanate, the protonic impurities present in DMI usually react with an isocyanate group, and so they work as short-stoppers. In consequence, a polymer having a suitable polymerization degree cannot be stably obtained.

Japanese Patent Laid-open Publication Nos. 90517/1986 and 204218/1986 disclose that substantially colorless polyamides having relative high molecular weight can be prepared by using DMI as a solvent. However, even according to these processes, the polyamides having a sufficiently high polymerization degree cannot be obtained, since the protonic impurities present in DMI react with the isocyanate group.

Thus, in such a case, it is necessary to remove the protonic impurities from DMI as much as possible.

As a technique for refining DMI, there is a distillation separation process, but since the above-mentioned impurities have about the same vapor pressure as DMI has, it is difficult to distill off substantially all of these impurities.

In fact, when commercially available DMI was further refined by distillation, it was hard to perfectly separate and remove the trace amounts of the above-mentioned impurities therefrom. For the perfect refining, it would be necessary to perform rectification in a great reflux ratio by the use of a multistage distillation column.

Moreover, when the distillation refining was carried out after the addition of an alkaline metal hydroxide such as sodium hydroxide or potassium hydroxide, or an acid such as sulfuric acid, phosphoric acid or oxalic acid, the effect of such an additive was not perceptible.

In addition, the refining process of using a prevalent adsorbent such as active carbon, zeolite ($Na_2Al_2Si_3O_{10}.xH_2O$), silica gel ($SiO_2.nH_2O$) or active china clay was tried, but it was impossible to selectively adsorb the above-mentioned impurities thereby, and the effect of such an adsorbent was not observed.

Accordingly, in order to sufficiently remove the protonic impurities from DMI, time and cost are required in large quantities.

SUMMARY OF THE INVENTION

An object of the present invention is to provide a process for refining DMI by which the above-mentioned impurities can be easily separated and removed therefrom at low cost.

Another object of the present invention is to provide a process for preparing an aromatic polyamide having a high polymerization degree by using DMI, as a reaction solvent, from which the impurities have been sufficiently removed.

The above first object of the present invention can be achieved by a process for refining 1,3-dimethyl-2-imidazolidinone which comprises the step of bringing 1,3-dimethyl-2-imidazolidinone into contact with a composite salt containing MgO and/or $SiO_2$ as a composition component.

The above second object of the present invention can be achieved by a process for preparing an aromatic polyamide which comprises the step of subjecting an aromatic diisocyanate and an aromatic dicarboxylic acid to thermal polycondensation in the presence of a catalyst in a 1,3-dimethyl-2-imidazolidinone solvent, the aforesaid process being characterized in that 1,3-dimethyl-2-imidazolidinone is previously brought into contact with a composite salt containing MgO and/or $SiO_2$ as a composition component, and afterward the thermal polycondensation is performed.

DESCRIPTION OF THE PREFERRED EMBODIMENTS

In the present invention, a composite salt is used. This composite salt functions as an adsorbent for various impurities such as biuret, urea, acetamide and N-methylformamide and contains at least one of MgO and $SiO_2$ as a composition component.

The composite salt used in the process of the present invention is an inorganic compound comprising at least one kind of composite salt which contains $SiO_2$ and/or MgO as a main component. The components of the above-mentioned composite salt are selected from the group consisting of alkaline metal oxides such as $Na_2O$, $K_2O$ and $Li_2O$, alkaline earth metal oxides such as CaO, MgO and BeO, amphoteric oxides such as $Al_2O_3$ and $B_2O_3$, and carbon group oxides such as $CO_2$ and $SiO_2$.

For example, the composite salt can be represented by the general formula $lMgO.mAl_2O_3.nSiO_2.xH_2O$ wherein each of l, m and n can take an optional value of 0 to 10. Typical examples of the composite salt are as follows:

$2MgO.Al_2O_3.xH_2O$ (l=2, m=1 and n=0)
$3MgO.Al_2O_3.xH_2O$ (l=3, m=1 and n=0)
$5MgO.Al_2O_3.xH_2O$ (l=5, m=1 and n=0)

$MgO.Al_2O_3.2SiO_2xH_2O$ (l=1, m=1 and n=2)
$2MgO.Al_2O_3.SiO_2.xH_2O$ (l=2, m=1 and n=1)
$MgO.3SiO_2.xH_2O$ (l=1, m=0 and n=3)
$2MgO.3SiO_2.xH_2O$ (l=2, m=0 and n=3) and
$Al_2O_39SiO_2.xH_2O$ (l=0, m=1 and n=9)

In addition, $Na_2O.Al_2O_3.3SiO_2.xH_2O$, $6MgO.Al_2O_3.CO_2.xH_2O$ and $CaO.SiO_2.xH_2O$ can be also used as the composite salt. These compounds can be used in the form of an optional combination, so long as the combination satisfies the above-mentioned conditions.

Each of these inorganic composite salts, when being in the state of its 4% by weight aqueous suspension, has a pH of 7.0 to 11.0, a bulk specific gravity of 10 to 60 ml/10 g, and a specific surface area of 50 to 400 $m^2/g$.

Moreover, each inorganic composite salt has either the ability to adsorb an alkali or the ability to adsorb an acid.

Although the composite salt used in the present invention has the ability to adsorb various impurities contained in DMI, the selectivity of the composite salt for these impurities depends upon a kind of composite salt itself. Therefore, the kind and the usage of the composite salt are suitably decided in accordance with kinds and contents of the impurities contained in DMI. For example, in the first place, when DMI contains acetamide, urea, NMF and the like of the above-mentioned impurities in large quantities, the composite salt containing at least $SiO_2$ and having alkali adsorbablility is preferably used.

Examples of such a composite salt include $Al_2O_3.9SiO_2.xH_2O$, $MgO.3SiO_2.xH_2O$, $2MgO.3SiO_2.xH_2O$, $Na_2O.Al_2O_3.3SiO_2.xH_2O$, $CaO.SiO_2.xH_2O$ and $MgO.Al_2O_3.2SiO_2.xH_2O$. In particular, the $SiO_2$-$Al_2O_3$ series composite salts are more preferable, since they have the high adsorbability for these impurities.

In the second place, when DMI contains impurities such as biuret in large quantities, the composite salt containing at least MgO and having acid adsorbablility is preferably used. Examples of such a composite salt include $6MgO.Al_2O_3.CO_2.xH_2O$, $MgO.3SiO_2.xH_2O$, $2MgO.3SiO_2.xH_2O$ and $3MgO.2Al_2O_3.xH_2O$. In particular, $MgO$-$Al_2O_3$ series composite salts are more preferable, since they have the high adsorbability for these impurities.

When all of the impurities contained in DMI and the removal of these impurities is intended, the composite salt containing at least MgO and $SiO_2$ and having alkali and acid adsorbability is preferably used. Examples of such a composite salt include $MgO.Al_2O_3.2SiO_2.xH_2O$, $MgO.3SiO_2.xH_2O$ and $2MgO.3SiO_2O$.

The above-mentioned first and second composite salts may be combined with each other to enable the removal of all the impurities. Furthermore, the above-mentioned composite salts may be mixed mutually in compliance with a use application.

For the purpose of contacting DMI with the composite salt in the process of the present invention, any method can be used, so long as it permits bringing DMI into contact with the composite salt by a certain means. As examples of such a contact method, there are "a standing method" in which both of DMI and the composite salt are placed in a vessel and they are then allowed to stand for a predetermined period of time; "a mixing method" in which the contents in the vessel are mixed; and "a column method" in which a predetermined amount of DMI is passed through a column filled with the composite salt. After contacting and refining, DMI can be easily separated from the composite salt by filtration. In the case that the column method is employed, the filtration step can be omitted.

The amount of the composite salt is usually in the range of 1 to 50 parts by weight based on 100 parts of DMI, but it may be suitably increased or decreased in accordance with the adsorbability of the selected composite salt.

In the present invention, a temperature in the contact treatment is preferably in the range of 5° to 180° C., more preferably in the range of 15° to 100° C. When the contact treatment temperature is less than 5° C., DMI would be frozen inconveniently, so that the ability of the composite salt cannot be exerted; when it is more than 180° C., the composite salt would be destroyed.

With regard to a period of time for the contact treatment, 10 minutes or more is enough, and when the contents in the vessel are mixed at a temperature of 80° C., the adsorption is substantially over in about 1 hour.

In DMI obtained under such conditions, the contents of urea, biuret, NMF and acetamide are as low as 10 ppm or less, and these impurities are not substantially detected by any analysis.

DMI from which the impurities have been removed by the refining process of the present invention is useful as a solvent for reactions of compounds each having an isocyanate group or the like. In addition, impurity-free DMI is also useful as a solvent for the reaction of producing a polyamic acid or a polyimide from an acid anhydride and an amine. In particular, DMI is useful as a solvent in preparing an aromatic polyamide.

Now, a preparation process of the aromatic polyamide according to the present invention will be described.

In the production process of the aromatic polyamide according to the present invention, any aromatic diisocyanate is usable as a monomer, so long as it does not contain any functional group active to carboxylic acids other than the diisocyanate groups. As exemplary aromatic diisocyanates, may be mentioned diisocyanates derived from biphenyl compounds, diisocyanates derived from diphenyl compounds, diisocyanates derived from naphthalene compounds, diisocyanates derived from phenyl compounds, etc. For example, as diisocyanates derived from biphenyl compounds, may be mentioned biphenyl-2,4'-diisocyanate, biphenyl-4,4'-diisocyanate, 3,3'-dimethylbiphenyl-4,4'-diisocyanate, 3,3'-dimethoxybiphenyl-4,4'-diisocyanate, and 2-nitrobiphenyl-4,4'-diisocyanate; as diisocyanates derived from diphenyl compounds, diphenylmethane-4,4'-diisocyanate, diphenylmethane-2,2'-diisocyanate, diphenylmethane-2,4'-diisocyanate, 3,3'-dichlorodiphenylmethane-4,4'-diisocyanate, 3,5-dimethyldiphenylmethane-4,4'-diisocyanate, 2,2'-dimethyldiphenylmethane-4,4'-diisocyanate, 3,3'-dimethyldiphenylmethane-4,4'-diisocyanate, 3-methoxydiphenylmethane-4,4'-diisocyanate, 2,4,6-trimethyldiphenylmethane-3,4'-diisocyanate, 2,2',5,5'-tetramethyldiphenylmethane-4,4'-diisocyanate, 3,3'-dimethoxydiphenylmethane-4,4'-diisocyanate, 4,4'-dimethoxydiphenylmethane-3,3'-diisocyanate, 4,4'-diethoxydiphenylmethane-3,3'-diisocyanate, 2,2'-dimethyl-5,5'-dimethoxydiphenylmethane-4,4'-diisocyanate, 3,3',5,5'-tetraisopropyldiphenylmethane-4,4'-diisocyanate, bis(4-isocyanatophenyl)dimethylmethane, bis(3-chloro-4-isocyanatophenyl)dimethylmethane, bis(4-isocyanatophenyl)ditrifluoromethylmethane, bis(4-isocyanatophenyl)ditrifluoromethylmethane, bis(4-isocyanatophenyl)-2-nitorphenylmethane, bis(4-isocyanatophenyl)-4-nitrophenylmethane, bis(4-isocyanate-2,5- dimethylphenyl)phenylmethane, bis(4-isocyanatophenyl)ethylene, bis(4-isocyanatophenyl)difluoroethylene, bis(4-isocyanatophenyl)cyclohexylmethane, bibenzyl-4,4-diisocyanate, bibenzyl-2,4-diisocyanate, diphenylether-4,4'-diisocyanate, and diphenylether-2,4'-diisocyanate; as diisocyanates derived from naphthalene compounds, naphthalene-1,4-diisocyanate, naphthalene-1,5-diisocyanate, 2-methylnaphthalene-1,5-diisocyanate, naphthalene-2,6-diisocyanate, naphthalene-2,7-diisocyanate, and 1,1'-dinaphthyl-2,2'-diisocyanate; and as diisocyanates derived from phenyl compounds, phenylene-1,2-diisocyanate, phenylene-1,3-diisocyanate, phenylene-1,4-diisocyanate, phenylene-2,4-diisocyanate, tolylene-2,4-diisocyanate, and tolylene-2,6-diisocyanate.

In particular, tolylene-2,4-diisocyanate, diphenylmethane-4,4'-diisocyanate, phenylene-1,4-diisocyanate, phenylene-1,3-diisocyanate and the like, which are available industrially, are often used. They may be used either singly or in combination.

Since these aromatic diisocyanates are apt to react with water, they are generally marketed in a sealed moisture-free state so that they can be used directly for polymerization.

The other monomer, i.e., the aromatic dicarboxylic acid is not always in the moisture-free state, when used as a raw material. Any aromatic compound can be used, so long as it has no functional group active to isocyanates other than the two carboxyl groups. Examples of the aromatic carboxylic acid include dicarboxylic acids derived from biphenyl compounds, dicarboxylic acids derived from diphenyl compounds, dicarboxylic acids derived from naphthalene compounds, dicarboxylic acids derived from phenyl compounds, etc. For example, may be mentioned as dicarboxylic acids derived from biphenyl compounds, biphenyl-2,4'-dicarboxylic acid, biphenyl-4,4'-dicarboxylic acid, 3,3'-dimethylbiphenyl-4,4'-dicarboxylic acid, 3,3'-dimethoxybiphenyl-4,4'-dicarboxylic acid, and 2-nitrobiphenyl-4,4'-dicarboxylic acid; as dicarboxylic acids derived from diphenyl compounds, diphenylmethane-4,4'-dicarboxylic acid, diphenylmethane-2,2'-dicarboxylic acid, diphenylmethane-2,4'-dicarboxylic acid, 3,3'-dichlorodiphenylmethane-4,4'-dicarboxylic acid, 3,5-dimethyldiphenylmethane-4,4'-dicarboxylic acid, 2,2'-dimethyldiphenylmethane-4,4'-dicarboxylic acid, 3,3'-dimethyldiphenylmethane-4,4'-dicarboxylic acid, 3-methoxydiphenylmethane-4,4'-dicarboxylic acid, 2,4,6-trimethyldiphenylmethane-3,4'-dicarboxylic acid, 2,2',5,5'-tetramethyldiphenylmethane-4,4'-dicarboxylic acid, 3,3'-dimethoxydiphenylmethane-4,4'-dicarboxylic acid, 4,4'-dimethoxydiphenylmethane-3,3'-dicarboxylic acid, 4,4'-diethoxydiphenylmethane-3,3'-dicarboxylic acid, 2,2'-dimethyl-5,5'-dimethoxydiphenylmethane-4,4'-dicarboxylic acid, 3,3',5,5'-tetraisopropyldiphenylmethane-4,4'-dicarboxylic acid, bis(4-carboxyphenyl)dimethylmethane, bis(3-chloro-4-carboxyphenyl)-dimethylmethane, bis(4-carboxyphenyl)ditrifluoromethylmethane, bis(4-carboxyphenyl)-2-nitrophenylmethane, bis(4-carboxyphenyl)-4-nitrophenylmethane, bis(4-carboxy-2,5-dimethylphenyl)phenylmethane, bis(4-carboxyphenyl)ethylene, bis(4-carboxyphenyl)difluoroethylene, bis(4-carboxyphenyl)cyclohexylmethane, bibenzyl-4,4'-dicarboxylic acid, bibenzyl-2,4'-dicarboxylic acid, diphenylether-4,4'-dicarboxylic acid, and diphenylether-2,4'-dicarboxylic acid; as dicarboxylic acids derived from naphthalene compounds, naphthalene-1,4-dicarboxylic acid, naphthalene-1,5-dicarboxylic acid, 2-methylnaphthalene-1,5-dicarboxylic acid, naphthalene-2,6-dicarboxylic acid, naphthalene-2,7-dicarboxylic acid, and 1,1'-dinaphthyl-2,2'-dicarboxylic acid; and as dicarboxylic acids derived from phenyl compounds, phenylene-1,2-dicarboxylic acid, phenylene-1,3-dicarboxylic acid, phenylene-1,4-dicarboxylic acid, tolylene-2,4-dicarboxylic acid, and tolylene-2,6-dicarboxylic acid. In particular, phenylene-1,2-dicarboxylic acid, phenylene-1,3-dicarboxylic acid, phenylene-1,4-dicarboxylic acid, tolylene-2,4-dicarboxylic acid and the like are often used. They may also be used either singly or in combination.

A catalyst used in the present invention is not particularly limited. Examples of the catalyst include known catalysts such as metallic alkoxides, cyclic phosphorus oxides, alkali metal salts, alkali metal carbonates and hydrogencarbonates of multivalent carboxylic acids, and alkali metal salts of alkali metal hydroxides. In particular, the alkali metal salts are preferred, and above all, alkali metal fluorides such as potassium fluoride and cesium fluoride are the preferable catalysts because of having high activity.

In the present invention, a molar ratio of the aromatic diisocyanate to the aromatic dicarboxylic acid is within the range of 0.70 to 1.30, and a molar ratio of 0.95 to 1.10 in the vicinity of a substantially equivalent amount is preferable.

In a preferable embodiment of the present invention, the aromatic dicarboxylic acid is first added to the refined DMI solvent prepared by the above-mentioned pretreatment, and bubbling of an inert gas is then performed in the solution under heating. Afterward, polymerization reaction is carried out dropping the aromatic diisocyanate.

The amount of the solvent is preferably 3 to 50 times as much as the total amount of the monomers, and it can be optionally adjusted in compliance with reaction conditions.

The inert gas which is blown into the solvent is not limited at all, so long as it is inert to the monomers and the solvent. Examples of the inert gas include nitrogen, argon and xenon, and they can be used singly or in combination. Above all, nitrogen is preferable in that it permits effective dehydration and is inexpensive. Thus, when nitrogen is used, moisture and low-boiling impurities can be easily removed from the system.

Commercially available DMI usually contains water in an amount of 100 to 300 ppm. In the present invention, the water content in DMI increases up to 1,000 ppm or more in the step of the pretreatment in some cases, depending upon a kind of composite salt. However, the water content therein decreases to a level of 20 ppm or less only by the bubbling of the inert gas in the solution under heating to which the heated aromatic dicarboxylic acid has been added. In blowing the inert gas into the solution, the temperature of DMI is set to 100° C. or more and is preferably in the range of 200° to 210° C. which are slightly lower than the boiling point of DMI itself.

In the present invention, the temperature of the polymerization reaction is preferably between 100° C. or more and the boiling point or less of the solvent. When the temperature is less than 100° C., the reaction is slow, so that the polymer having high molecular weight cannot be obtained. The particularly preferable temperature of the polymerization is in the range of 150° to 200° C. at which solution polymerization is possible. The time of the polymerization reaction is preferably between 30 minutes to 5 hours, and the reaction should be brought to an end at the point of time when the generation of the by-product carbon dioxide has not been observed substantially.

The aromatic polyamide thus obtained by the present invention is then spun to prepare a fiber having high strength, and therefore it is suitable for the manufacture of various fiber products. In addition, when used alone or together with other resins, the aromatic polyamide can be utilized for various applications such as the manufacture of films, sheets and paper products.

Now the present invention will be described in detail in reference to examples.

With regard to performance of composite salts as adsorbents, contents of impurities in DMI and physical properties of obtained polymers, measurements were made as follows:

Alkali Adsorbability

To 200 g of a 0.4% KOH-DPG (dipropylene glycol) solution was added 2 g of a selected adsorbent, and the solution was then stirred at 95° C. for 30 minutes. Afterward, the solution was filtered through a glass filter. After cooling, 40 g of the filtrate was sampled, and 100 ml of refined water was then added thereto. Next, pH of the solution was measured, and the solution was then titrated with a 0.05 N-HCl solution until a pH of 7.8 had been reached. Similarly, a blank test was carried out.

*Alkali adsorbability (mg eq.-*
$$KOH/g) = (X_1/S_1 - X_2/S_2) \times 0.05 \times f(HCl) \times 200 \times \tfrac{1}{4}$$

$S_1$ = an amount (g) of a blank sample,
$X_1$ = milliliters of HCl consumed in a blank sample,
$S_2$ = an amount (g) of a filtrate sample, and
$X_2$ = milliliters of HCl consumed by the filtrate sample.

Acid Adsorbability

To 100 g of a 0.05N dioctyl phthalate solution was added 0.5 g of an adsorbent, and the solution was then stirred at 85° C. for 70 minutes. Afterward, the solution was filtered through a glass filter, and after cooling, 40 g of the filtrate was sampled. Next, 50 ml of ethyl alcohol was added thereto, and 5 drops of a phenolphthalein indicator were further added thereto. The solution was then titrated with a 0.1 N-KOH solution until the solution had assumed a light red color.

Similarly, a blank test was carried out.

*Acid adsorbability*
$$(mEq/g) = [2.5 \times (B-X) \times f \times 0.1]/0.5$$

$B$ = an amount (ml) of a 0.1 N-KOH solution consumed in a blank test,
$X$ = an amount (ml) of the 0.1 N-KOH solution consumed in titration, and
$f$ = factor of 0.1 N-KOH solution.

Specific Surface Area

A specific surface area (m²/g) was measured in accordance with a BET method.

Acetamide, NMF, Biuret and Urea

Analysis was made by the use of a high-performance liquid chromatograph (hereinafter referred to simply as HPLC).

Conditions for analysis:
column: YMC Pack A-312 ODS (made by Yamamura, Chemical Laboratories)
temperature: room temperature,
flow rate: 0.8 ml/minute,
mobile phase: acetonitrile 3%, aqueous phosphoric acid buffer solution PH=2.33, and
detector: UV detector (205 nm).

Peaks were detected at RT (retention time)=4.2 minutes for acetamide, RT=3.6 minutes for urea, RT=4.3 minutes for biuret and RT=4.5 minutes for NMF, and caliblation curves were made to calculate absolute amounts. The lower limit of the detection was 10 ppm.

Inherent Viscosity ($\eta$inh)

Inherent viscosity $(\eta inh) = [l_n(t/t_0)]/c$
$t_0$ = down flow time of a solvent in a viscometer,
$t$ = down flow time of a dilute polymer solution in the same solvent in the same viscometer, and
$c$ = concentration (grams) of polymer solid content in 100 ml of the solvent.

The polymer solid content (c) in the polymer solution was calculated from amounts of the monomers added to the solvent, and the down flow time (t) was measured at a temperature of 30° C., after the polymer had been diluted with N-methylpyrrolidone so that the concentration of the polymer solid content might be 0.1 g per 100 ml of the solvent.

Moisture in the solvent and the solution was measured at room temperature by means of a Karl Fischer's moisture meter (made by Kyoto Electronics Co., Ltd.; MK-210; electrical quantity titration system).

Average Molecular Weight

A polymer solution was diluted with dimethylformamide, and the peak of a molecular weight distribution curve was then measured by the use of GPC. Afterward, an average molecular weight of the polymer was obtained on the basis of a polystyrene standard.

Viscosity

A polymer solution was kept overnight in a thermostatic chamber at 23° C., and afterward the viscosity of the polymer solution was measured by the use of a usual BH viscometer.

EXAMPLE 1-A

In a 2-liter reaction vessel equipped with a stirrer and a thermometer was placed 1.5 kg of commercially available DMI (containing 150 ppm of acetamide, 60 ppm of NMF and 500 ppm of urea), and 45 g (3% by weight of DMI) of an $SiO_2$-$Al_2O_3$ series composite salt ($Al_2O_3$·9$SiO_2$·x$H_2O$; made by Tomita Pharmaceutical Co., Ltd.; Tomix AD-700; 13% of $Al_2O_3$ and 69% of $SiO_2$; pH=7.5; bulk specific gravity=25 ml/10 g; specific surface area=150 m²/g; and alkali adsorbability=3.4 mEq/g) was further added thereto. Afterward, the solution was stirred for 1 hour while maintained at 80° C. After cooling, the composite salt was removed therefrom by filtration under reduced pressure, so that 1.45 kg of refined DMI was obtained (recovery=96.7%).

As the result of analysis by HPLC, it was apparent that the amounts of acetamide, NMF and urea were less than detection limit.

EXAMPLE 2-A

In the same reaction vessel as used in Example 1 was placed 1.5 kg of DMI (containing 120 ppm of biuret), and 75 g (5% by weight of DMI) of an MgO-Al$_2$O$_3$ series composite salt (6MgO.Al$_2$O$_3$.CO$_2$.xH$_2$O; made by Tomita Pharmaceutical Co., Ltd.; Tomix AD-570; 17.2% of Al$_2$O$_3$, 37.4% of MgO and 8.1% of CO$_2$; pH=8.7; bulk specific gravity=30 ml/10 g; specific surface area=150 m$^2$/g; and acid adsorbability= 4.2 mEq/g) was further added thereto. Afterward, the solution was stirred for 2 hours while maintained at 50° C. After cooling, the composite salt was separated and removed therefrom by filtration, so that 1.42 kg of refined DMI was obtained (recovery=94.7%).

As the result of analysis by HPLC, it was apparent that the amount of biuret were less than detection limit.

EXAMPLE 3-A

In the same reaction vessel as used in Example 1 was placed 1.5 kg of DMI (containing 130 ppm of acetamide, 120 ppm of NMR, 350 ppm of urea and 02 ppm of biuret); and 150 g (10% by weight of DMI) of an SiO$_2$-MgO series composite salt (2MgO.3SiO$_2$.xH$_2$O; made by Kyowa Chemical Industry Co., Ltd.; Kyoward 601; 65.1% of SiO$_2$ and 13.6% of MgO; pH=10.0; bulk specific gravity=27.4 ml/10 g; specific surface area=150 m$^2$/g; alkali adsorbability=3.4 mEq/g; and acid adsorbability=2.5 mEq/g) was further added thereto. Afterward, the solution was stirred for 3 hours while maintained at 80° C. After cooling, the composite salt was separated and removed therefrom by filtration, so that 1.35 kg of refined DMI was obtained (recovery=86.7%).

As the result of analysis by HPLC, it was apparent that the amounts of all the impurities were less than detection limit.

EXAMPLE 4-A

The same DMI, reaction vessel and procedure as used in Example 3-A were employed with the exception that an inorganic adsorbent was a mixture of 45 g of an SiO$_2$-Al$_2$O$_3$ series composite salt (Al$_2$O$_3$.9SiO$_2$.xH$_2$O; 3% by weight of DMI) and 45 g of an MgO-Al$_2$O$_3$ series composite salt (6MgO.Al$_2$O$_3$.CO$_2$.xH$_2$O; 3% by weight of DMI), so that 1.40 kg of DMI was obtained (recovery=93.3%).

As a result of analysis of HPLC, it was apparent that the amounts of all the impurities were less than detection limit.

EXAMPLE 5

Two columns filled with 500 g of an SiO$_2$-Al$_2$O$_3$ series composite salt (Al$_2$O$_3$.9SiO$_2$. xH$_2$O) and 500 g of an MgO-Al$_2$O$_3$ series composite salt (6MgO.Al$_2$O$_3$.CO$_2$.xH$_2$O), respectively, were connected to each other in a two-step form in series, and 20.0 kg of DMI used in Example 3 was passed through these columns at room temperature (20° C.) at a flow rate of 1.5 kg/hr, so that 18.5 kg of DMI was obtained (recovery=92.5%). As a result of analysis by HPLC, it was apparent that the amounts of all the impurities were less than detection limit.

EXAMPLE 6

10.0 kg of DMI used in Example 3 was passed through a column filled with a mixture of 250 g of an SiO$_2$-Al$_2$O$_3$ series composite salt (Al$_2$O$_3$.9SiO$_2$. xH$_2$O) and 250 g of an MgO-Al$_2$O$_3$ series composite salt (2.5MgO.Al$_2$O$_3$.xH$_2$O; made by Kyowa Chemical Industry Co., Ltd.; Kyoward 300; 26.4% of MgO and 26.3% of Al$_2$O$_3$; pH=8.3; bulk specific gravity=37.3 ml/10 g; specific surface area=130 m$^2$/g; and acid adsorbability=3.4 mEq/g) at room temperature (20° C.) at a flow rate of 1.5 kg/hr, so that 9.1 kg of DMI was obtained (recovery=91.0%). As a result of analysis by HPLC, it was apparent that the amounts of all the impurities were less than detection limit.

EXAMPLE 7

The same procedure as in Example 1 was repeated with the exception that DMI and the composite salt used in Example 1 were allowed to stand at room temperature (20° C.) for 3 hours without stirring them, and the used composite salt was then separated and removed therefrom by filtration, so that 1.43 kg of DMI was obtained (recovery 95.3%). As a result of analysis by HPLC, it was apparent that the amounts of all the impurities were less than detection limit.

EXAMPLES 1-B TO 4-C

Experiments in Examples 1-B to 1-D were carried out by the use of the same DMI, apparatus and procedure as in Example 1-A with the exception that inorganic composite salts and treatment conditions (amounts of the composite salts, treatment temperature and treatment time) were changed. Similarly, Examples 2-B to 2-D, Examples 3-B and 3-C and Examples 4-B and 4-C were carried out as in Example 2-A, Example 3-A and Example 4-A, respectively. The results are set forth in Table 1.

In this connection, Table 2 shows compositions, contents of components and adsorbabilities (alkali adsorbability and acid adsorbability) of the composite salts used in Examples 1-B to 4-C.

TABLE 1

| | Content (ppm) of Impurity in DMI before Treatment | | | | Composition Formula |
|---|---|---|---|---|---|
| | Acetamide | NMF | Urea | Buiret | of Composite Salts |
| Example 1-B | 150 | 60 | 500 | 10> | Na$_2$O.Al$_2$O$_3$.3SiO$_2$.xH$_2$O |
| Example 1-C | " | " | " | " | MgO.Al$_2$O$_3$.2SiO$_2$.xH$_2$O |
| Example 1-D | 10> | 10> | 10> | 120 | MgO.3SiO$_2$.xH$_2$O |
| Example 2-B | " | " | " | " | 3MgO.2Al$_2$O$_3$.xH$_2$O |
| Example 2-C | " | " | " | " | MgO.Al$_2$O$_3$.2SiO$_2$.xH$_2$O |
| Example 2-D | " | " | " | " | 2MgO.3SiO$_2$.xH$_2$O |
| Example 3-B | 130 | 120 | 350 | 92 | " |
| Example 3-C | " | " | " | " | MgO.3SiO$_2$.xH$_2$O |
| Example 4-B | " | " | " | " | Al$_2$O$_3$.9SiO$_2$.xH$_2$O/ 3MgO.2Al$_2$O$_3$.xH$_2$O = 1:1 |
| Example 4-C | " | " | " | " | Na$_2$O.Al$_2$O$_3$.3SiO$_2$.xH$_2$O/ |

TABLE 1-continued $6MgO.Al_2O_3.CO_2.xH_2O = 1:2$

| | Treatment Conditions | | | Content (ppm) of Impurity in DMI after Treatment | | | |
|---|---|---|---|---|---|---|---|
| | Amount of Composite Salt (wt %) | Temperature (°C.) | Time (hr) | Acetamide | NMF | Urea | Biuret |
| Example 1-B | 5 | 100 | 3 | 10> | 10> | 10> | 10> |
| Example 1-C | 4 | 50 | 1.5 | " | " | " | " |
| Example 1-D | 10 | 30 | 3 | " | " | " | " |
| Example 2-B | 7 | 50 | 1 | " | " | " | " |
| Example 2-C | 7 | 30 | 3 | " | " | " | " |
| Example 2-D | 10 | 30 | 3 | " | " | " | " |
| Example 3-B | 20 | 30 | 3 | " | " | " | " |
| Example 3-C | 20 | 30 | 3 | " | " | " | " |
| Example 4-B | 10 | 80 | 2 | " | " | " | " |
| Example 4-C | 10 | 80 | 3 | " | " | " | " |

TABLE 2

| Composition Formula of Composite Salt | Composition of Composite Salt (wt %) | | | | | Physical Properties of Composite Salt | | Adsorbability (mEq/g) | |
|---|---|---|---|---|---|---|---|---|---|
| | $SiO_2$ | $Al_2O_3$ | MgO | others | pH | Bulk Specific Gravity (ml/10 g) | Specific Surface Area ($m^2/g$) | Acid | Alkali |
| $MgO.Al_2O_3.2SiO_2.xH_2O$ | 30.5 | 31.0 | 13.2 | 25.3 | 9.3 | 30 | 300 | 2.3 | 3.2 |
| $MgO.3SiO_2.xH_2O$ | 63.2 | — | 14.1 | 22.7 | 10.0 | 30 | 270 | 2.1 | 3.4 |
| $Na_2O.Al_2O_3.3SiO_2.xH_2O$ | 75.0 | 6.8 | — | 18.2 | 8.3 | 50 | 130 | 2.2 | 3.3 |
| $3MgO.Al_2O_3.xH_2O$ | — | 38.0 | 22.9 | 39.1 | 9.6 | 27 | 130 | 3.2 | — |

COMPARATIVE EXAMPLE 1

Following the same procedure as in Example 1-A with the exception that the $SiO_2$-$Al_2O_3$ composite salt was replaced with silica gel (WakoGel C-300; $SiO_2$), purification was carried out. As a result of anyalysis by HPLC, it was apparent that 145 ppm of acetamide, 50 ppm of NMF and 460 ppm of urea were present in the purifed product, which was indicative that the effect of the impurity removal was insufficient.

COMPARATIVE EXAMPLE 2

Following the same procedure as in Example 2-A with the exception that the MgO-$Al_2O_3$ composite salt was replaced with MgO powder (guaranteed reagent), purification was carried out. As a result of anyalysis by HPLC, it was apparent that 120 ppm of biuret was present in the purifed product, which was indicative that the effect of the impurity removal was not perceived.

Next, DMI which had been purified in the abovementioned examples was used to prepare aromatic polyamides.

EXAMPLE 8

In a 1-liter reaction vessel equipped with a stirrer, a thermometer, a condenser, a dropping funnel and a nitrogen intake pipe were place 740 g of DMI prepared in Example 1-A and 34.2 g of terephthalic acid (0.206 mol) in a nitrogen atmosphere, and a nitrogen gas was introduced thereinto with stirring, followed by heating the solution to 200° C. Heating was further continued for 1 hour under nitrogen bubbling.

Afterward, 0.123 g (1.0 mol% with respect to terephthalic acid) of potassium fluoride powder which had been dried at 150° C. for 15 hours was added thereto in a nitrogen atmosphere, and 35.8 g (0.206 mol) of tolylene-2,4-diisocyanate was continuously added dropwise thereto over 1.5 hours through the dropping funnel. After the dropping, the solution was maintained at 200° C. for 30 minutes and was then cooled to room temperature, thereby obtaining a light yellow polymer solution.

With regard to the thus obtained polymer solution, viscosity was 47 poise, inherent viscosity ($\eta$inh) was 1.83, and average molecular weight was 260,000.

Afterward, this polymer solution was extruded into a coagulating bath (DMF/$CaCl_2$/water) at 50° C. through a usual wet spinning machine, and at this time, it could be spun without cutting the resulting thread. After drying and stretching, the thread having 2 deniers was obtained. Strength of the thread was 5 g/denier.

COMPARATIVE EXAMPLE 3

Following the same procedure as in Example 8 with the exception that commercially available DMI used in Example 1-A was employed as a raw material, polymerization was performed, thereby obtaining a light yellow polymer solution. With regard to the thus obtained polymer solution, viscosity was as low as 8 poise, inherent viscosity ($\eta$inh) was at a low level of 1.2, and average molecular weight was also low, 177,000.

This polymer solution was spun in the same manner as in Example 8, but thread was cut, which made spinning impossible.

EXAMPLE 9

In a 1-liter reaction vessel equipped with a stirrer, a thermometer, a condenser, a dropping funnel and a nitrogen intake pipe were placed 800 g of DMI prepared in Example 2-A and 33.2 g (0.200 mol) of terephthalic acid in a nitrogen atmosphere, and a nitrogen gas was then introduced thereinto with stirring, followed by heating the solution to 200° C. Heating was further continued for 1 hour under nitrogen bubbling, thereby distilling 80 g of DMI. In the solution in the reaction vessel, water was present in an amount of 20 ppm or less.

Afterward, 120 g (1.0 mol% with respect to terephthalic acid) of potassium fluoride powder which had been dried at 150° C. for 15 hours was added thereto in a nitrogen atmosphere, and temperature rise was then performed up to 200° C. with stirring. While nitrogen was blown into the DMI solution in the reaction vessel and while the temperature of the solution was maintained at 200° C., 34.8 g (0.20 mol) of tolylene-2,4-diisocyanate was continuously added dropwise thereto over 1.5 hours through the dropping funnel. After the dropping, the solution was maintained at 200° C. for 30 minutes and was then cooled to room temperature, thereby obtaining a light yellow polyamide solution.

With regard to the thus obtained polymer solution, viscosity was 55 poise, inherent viscosity ($\eta$inh) was 1.87, and average molecular weight was 280,000.

Afterward, this polymer solution was extruded into an aqueous DMI solution at 50° C. through a usual wet spinning machine, and at this time, it could be spun without cutting the resulting thread. After drying and stretching, the thread having 2 deniers was obtained. Strength of the one thread was 6 g/denier.

What is claimed is:

1. A process for preparing an aromatic polyamide which comprises the step of subjecting an aromatic diisocyanate and an aromatic dicarboxylic acid to thermal polycondensation in the presence of a catalyst and a 1,3-dimethyl-2-imidazolidinone solvent, said process being characterized in that said 1,3-dimethyl-2-imidazolidinone solvent has been previously refined by contacting said solvent with an adsorbent composite salt comprising at least two composition components selected from the group consisting of MgO, $SiO_2$ and $Al_2O_3$, and afterward said thermal polycondensation is performed.

2. A process according to claim 1 wherein said composite salt is at least one selected from the group consisting of $2MgO.Al_2O_3.xH_2O$, $3MgO.Al_2O_3.xH_2O$, $5MgO.Al_2O_3.xH_2O$, $MgO.Al_2O_3.2SiO_2.xH_2O$, $2MgO.Al_2O_3.SiO_2.xH_2O$, $MgO.3SiO_2.xH_2O$, $2MgO.3SiO_2.xH_2O$ and $Al_2O_3.9SiO_2.xH_2O$.

3. A process according to claim 1 wherein said composite salt is used in an amount of 1 to 50 parts by weight based on 100 parts by weight of 1,3-dimethyl-2-imidazolidinone.

4. A process according to claim 1 wherein said composite salt has a pH of 7.0 to 11.0 in the state of a 4% by weight aqueous suspension.

5. A process according to claim 1 wherein said composite salt has a bulk specific gravity of 10 to 60 ml/10 g.

6. A process according to claim 1 wherein said composite salt has a specific surface area of 50 to 400 m²/g.

7. A process according to claim 1 wherein when brought into contact with said composite salt, 1,3-dimethyl-2-imidazolidinone has a temperature of 5° to 180° C.

8. A process according to claim 1 wherein after 1,3-dimethyl-2-imidazolidinone has been brought into contact with said composite salt, an inert gas is bubbled through the solvent while heating.

9. A process according to claim 1 wherein the amount of 1,3-dimethyl-2-imidazolidinone is 3 to 50 times as much as the total amount of said aromatic diisocyanate and said aromatic dicarboxylic acid.

10. A process for preparing an aromatic polyamide which comprises the step of subjecting an aromatic diisocyanate and an aromatic dicarboxylic acid to thermal polycondensation in the presence of a catalyst and a 1,3-dimethyl-2-imidazolidinone solvent, said process being characterized in that said 1,3-dimethyl-2-imidazolidinone solvent has been previously refined by contacting said solvent with a hydrated adsorbent composite salt, wherein said composite salt is selected from the group consisting of (a) a hydrated composite salt comprising $SiO_2$ and MgO, and (b) a hydrated composite salt comprising at least one component selected from the group consisting of $SiO_2$ and MgO and at least one second component selected from the group consisting of alkaline metal oxides, alkaline earth metal oxides, amphoteric oxides and carbon group oxides, and afterward said thermal polycondensation is performed.

11. The process of claim 10 wherein said alkaline metal oxide is selected from the group consisting of $Na_2O$, $K_2O$ and $Li_2O$.

12. The process of claim 10 wherein said alkaline earth metal oxide is selected from the group consisting of CaO, MgO and BeO.

13. The process of claim 10 wherein said amphoteric oxide is selected from the group consisting of $Al_2O_3$ and $B_2O_3$.

14. The process of claim 10 wherein said carbon group oxide is selected from the group consisting of $CO_2$ and $SiO_2$.

15. The process of claim 10 wherein the composite salt is represented by the formula $lMgO.mAl_2O_3.nSiO_2.xH_2O$, wherein l, m and n are integers of 0 to 10 with the proviso that at least two of l, m and an are 1 or greater.

16. The process of claim 10 wherein the composite salt is selected from the group consisting of $Na_2O.Al_2O_3.3SiO_2.xH_2O$, $6MgO.Al_2O_3.CO_2xH_2O$, $CaO.SiO_2.xH_2O$, $Al_2O_3.9SiO_2.xH_2O$, $MgO.Al_2O_3.2SiO_2.xH_2O$, and $3MgO.Al_2O_3.xH_2O$.

17. A process for preparing an aromatic polyamide comprising the steps of heating an aromatic diisocyanate and an aromatic dicarboxylic acid in the presence of a polycondensation catalyst and refined 1,3-dimethyl-2-imidazolidinone solvent, wherein said heating step is at a temperature sufficient to promote thermal polycondensation, and wherein said 1,3-dimethyl-2-imidazolidinone is refined by bringing, 1,3-dimethyl-2-imidazolidinone into contact with a composite salt containing at least two composition components selected from the group consisting of MgO, $SiO_2$ and $Al_2O_3$.

18. A process for preparing an aromatic polyamide comprising the step of heating reactants comprising an aromatic diisocyanate and an aromatic dicarboxylic acid in the presence of polycondensation catalyst and refined 1,3-dimethyl-2-imidazolidinone solvent, wherein said heating step is at a temperature sufficient to promote polycondensation, and wherein said 1,3-dimethyl-2-imidazolidinone solvent is a refined solvent prepared by contacting 1,3-dimethyl-2-imidazolidinone with a hydrated composite salt, wherein said composite salt is selected from the group consisting of (a) a hydrated composite salt comprising $SiO_2$ and MgO, and (b) a hydrated composite salt comprising at least one first component selected from the group consisting of $SiO_2$ and MgO and at least one second component selected from the group consisting of alkaline metal oxides, alkaline earth metal oxides, amphoteric oxides and carbon group oxides.

* * * * *